(12) United States Patent
Schönbeck et al.

(10) Patent No.: US 7,189,518 B2
(45) Date of Patent: Mar. 13, 2007

(54) SOLUBLE CD40L(CD154) AS A PROGNOSTIC MARKER OF ATHEROSCLEROTIC DISEASES

(75) Inventors: Uwe Schönbeck, Randolph, MA (US); Paul Ridker, Chestnut Hill, MA (US); Peter Libby, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 49 days.

(21) Appl. No.: 10/288,253

(22) Filed: Nov. 5, 2002

(65) Prior Publication Data

US 2003/0152566 A1 Aug. 14, 2003

Related U.S. Application Data

(60) Provisional application No. 60/338,841, filed on Nov. 5, 2001.

(51) Int. Cl.
*G01N 33/53* (2006.01)
(52) U.S. Cl. ...................................... 435/7.1
(58) Field of Classification Search .............. 435/4, 435/29
See application file for complete search history.

(56) References Cited

U.S. PATENT DOCUMENTS

| | | | |
|---|---|---|---|
| 6,117,642 A | 9/2000 | Crow et al. | |
| 6,369,065 B1 | 4/2002 | Chatelain et al. | |

FOREIGN PATENT DOCUMENTS

| | | |
|---|---|---|
| WO | WO 98/20155 | 5/1998 |
| WO | WO 98/43630 | 10/1998 |
| WO | WO 01/15744 A1 | 3/2001 |

OTHER PUBLICATIONS

Aukrust et al, "Circulation", V. 100, pp. 614-620, 1999.*
Koenig et al, "Circulation", V.99, pp. 237-242, 1999.*
Koenig, Wolfgang, Ital. Heary J, V. 2(3), pp. 157-163 (2001).*
Aukrust, Pål et al., "Enhanced Levels of Soluble and Membrane-Bound CD40 Ligand in Patients With Unstable Angina," *Circulation*, 1999, vol. 100, pp. 614-620.
Brignole, F. et al., "Flow Cytometric Analysis of Inflammatory Markers in KCS: 6-Month Treatment With Topical Cyclosporin A," *Invest Opthalmol Vis Sci.*, Jan. 2001; vol. 42, No. 1, pp. 90-95.
di Marzio, P. et al., "Soluble CD40 Ligand Induces β-chemokines Production by Macrophage and Resistance to HIV-1 Entry," *Cytokine*, Oct. 2000, vol. 12, No. 10, pp. 1489-1495.
Foy, Theresa M. et al., "Immune Regulation By CD40 and its Ligand GP39," *Annu. Rev. Immunol.* 1996, vol. 14, pp. 591-617.
Henn, V. et al., "CD40 Ligand on Activated Platelets Triggers an Inflammatory Reaction of Endothelial Cells," *Nature*, Feb. 5, 1998, vol. 391, No. 6667, pp. 591-594.
International Search Report for PCT/US02/35505, Date of completion of international search: Aug. 18, 2003.
Kornbluth, Richard et al., "CD40 Ligand (CD154) Stimulation of Macrophages to Produce HIV-1-Suppressive β-chemokines," Proc. Natl. Acad. Sci, Apr. 1998, vol. 95, pp. 5205-5210.
Mach, François et al., "Activation of Monocyte/Macrophage Functions Related to Acute Atheroma Complication by Ligation of CD40," *Circulation*, 1997, vol. 96, pp. 396-399.
Mach, François et al., "T Lymphocytes Induce Endothelial Cell Matrix Metalloproteinase Expression by a CD40L-Dependent Mechanism," *American Journal of Pathology*, Jan. 1999, vol. 154, No. 1, pp. 229-238.
Phipps, Richard P., "Atherosclerosis: The Emerging Role of Inflammation and the CD40—CD40 Ligand System," *PNAS*, Jun. 20, 2000, vol. 97, No. 13, pp. 6930-6932.
Schönbeck, U. et al., "CD40 Ligation Induces Tissue Factor Expression in Human Vascular Smooth Muscle Cells," *American Journal of Pathology*, Jan. 2000, vol. 156, No. 1, pp. 7-14.
Schönbeck, U. et al., "Inhibition of CD40 Signaling Limits Evolution of Established Atherosclerosis in Mice," *PNAS*, Jun. 20, 2000, vol. 97, No. 13, pp. 7458-7463.
Szabolcs, M.J. et al., "Analysis of CD154 and CD40 Expression in Native Coronary Atherosclerosis and Transplant Associated Coronary Artery Disease," *Virchows Arch.*, Aug. 2000, vol. 437, No. 2, pp. 149-159.
Bogaert, M., et al., "Gecommentrarieerd geneesmiddelenrepertorium 2001", Belgisch Centrum Vor Farmacotherapeutische Informatie, XP 002361328.
Elwood, P.C., "Aspirin in the Prevention of Myocardial Infarction Current Status," *Drugs*, vol. 28, pp. 1-5 (1984).
Schonebeck, U., et al., "Soluble CD40L and Cardiovascular Risk in Women," *Circulation*, vol. 104, pp. 2266-2268 (2001).
Varo, Nerea, et al., "Elevated sCD40L plasma concentrations in women correlates to enhanced relative risk of future cardiovascular events," *Circulation*, vol. 104, No. 17 Supplement, pp. II. 779 (2001).

* cited by examiner

*Primary Examiner*—Christopher R. Tate
*Assistant Examiner*—Amanda P. Wood
(74) *Attorney, Agent, or Firm*—Wolf, Greenfield & Sacks, P.C.

(57) ABSTRACT

This invention involves the new use of a diagnostic test to determine the risk of atherosclerotic diseases such as myocardial infarction and stroke, particularly among individuals with no signs or symptoms of current disease and among nonsmokers. Further, this invention involves the new use of a diagnostic test to assist physicians in determining which individuals at risk will preferentially benefit from certain treatments designed either to prevent first or recurrent myocardial infarctions and strokes, or to treat acute and chronic cardiovascular disorders. Methods for treatment also are described.

10 Claims, 1 Drawing Sheet

SOLUBLE CD40L(CD154) AS A PROGNOSTIC MARKER OF ATHEROSCLEROTIC DISEASES

RELATED APPLICATIONS

This application claims priority under 35 U.S.C. §119(e) from U.S. Provisional Application Ser. No. 60/338,841, filed Nov. 5, 2001, and entitled: SOLUBLE CD40L(CD154) AS A PROGNOSTIC MARKER OF ATHEROSCLEROTIC DISEASES incorporated herein in its entirety by reference.

GOVERNMENT SUPPORT

The work leading to the present invention was funded in part by grant numbers HL-34636, HL-56985, HL-58755, 1L-63293 from the National Heart, Lung and Blood Institute. Accordingly, the United States Government may have certain rights to this invention.

FIELD OF THE INVENTION

This invention describes the new use of a diagnostic test to determine the risk of cardiovascular disorders, such as myocardial infarction and stroke, particularly among individuals with no signs or symptoms of current disease and among nonsmokers. Further, this invention describes the new use of a diagnostic test to assist physicians in determining which individuals at risk will preferentially benefit from certain treatments designed to prevent or treat cardiovascular disorders. Methods for treatment also are described.

BACKGROUND OF THE INVENTION

Despite significant advances in therapy, cardiovascular disease remains the single most common cause of morbidity and mortality in the developed world. Thus, prevention of cardiovascular disorders such as myocardial infarction and stroke is an area of major public health importance. Currently, several risk factors for future cardiovascular disorders have been described and are in wide clinical use in the detection of individuals at high risk. Such screening tests include evaluations of total and HDL cholesterol levels. However, a large number of cardiovascular disorders occur in individuals with apparently low to moderate risk profiles, and our ability to identify such patients is limited. Moreover, accumulating data suggests that the beneficial effects of certain preventive and therapeutic treatments for patients at risk for or known to have cardiovascular disorders differs in magnitude among different patient groups. At this time, however, data describing diagnostic tests to determine whether certain therapies can be expected to be more or less effective are lacking.

Certain cardiovascular disorders, such as myocardial infarction and ischemic stroke, are associated with atherosclerosis. The mechanism of atherosclerosis is not well understood. CD40 ligand (also known as CD40L, CD154, and/or gp39) is a 261 amino acid, type II transmembrane protein. One or more biologically active soluble forms of the molecule, collectively designated sCD40L, are produced by proteolytic cleavage of the full-length form, which may occur intracellularly or on the cell surface.

CD40L is a multipotent immunomodulator that together with its receptor, CD40, are expressed on a broad variety of cells including vascular endothelial (EC) and smooth muscle cells (SMC), mononuclear phagocytes (MØ), and platelets. Engagement of the CD40 receptor on any of the foregoing cell types, reportedly triggers the expression of various pro-inflammatory mediators, such as the cytokines IL1, IL-6, IL-12, TNFα, or IFNγ, the chemokines IL-8, MCP-1, or RANTES, the adhesion molecules ICAM-1 or VCAM-1, the matrix metalloproteinases MMP-1/-2/-3/-7/-8/-9/-10/-11/-12/-13, as well as the procoagulant tissue factor. Expression of these pro-inflammatory mediators has been, reportedly, linked to the promotion of a wide array of pro-atherogenic functions in vitro. These observations have implicated CD40L in the various stages of atherogenesis.

Elevated levels of sCD40L have been described among patients with unstable angina. Further, concentrations of sCD40L in serum or other body fluids have been used to assess the immune, inflammatory, or malignant status of human patients. Such patients include patients suffering from systemic autoimmunity or inflammation, vascular diseases, viral diseases, or malignancies, or patients undergoing immunosuppressive therapy. These patients are not healthy individuals. Since levels of sCD40L increase during inflammation, it has been uncertain whether statistical associations observed in these prior studies of acutely ill or high-risk populations are causal, are due to short-term inflammatory changes or are due to interrelations with other risk factors, in particular, smoking and hyperlipidemia.

Elevated levels of markers of inflammation have been shown previously to be predictive of future adverse cardiovascular disorders. This has not previously been demonstrated for sCD40L, a mediator of certain aspects of inflammation although not conventionally regarded previously as a systemic marker of inflammation.

SUMMARY OF THE INVENTION

This invention describes in one aspect new diagnostic tests which broadly include (1) the prediction of risk of future cardiovascular disorders such as myocardial infarction and stroke and peripheral arterial disease; and (2) the determination of the likelihood that certain individuals will benefit to a greater or lesser extent from the use of certain treatments designed to prevent and/or treat cardiovascular disorders. These new tests are based in part upon the following discoveries.

It has been discovered that elevated levels of sCD40L are predictive of future cardiovascular disorders. For example, elevated levels of sCD40L in apparently healthy, nonsmokers are predictive of an increased risk of myocardial infarction. As another example, elevated levels of sCD40L are predictive of an increased likelihood of a future stroke.

It has been discovered also that the likelihood that certain individuals will benefit to a greater or a lesser extent from the use of certain therapeutic agents for reducing the risk of a future cardiovascular disorder can be determined from the base-line level sCD40L in an individual. The invention is based in part on the surprising discovery that that sCD40L has a predictive value independent of other predictors of future cardiovascular disorders. In particular, sCD40L predicts future adverse cardiovascular disorders independent of the systemic inflammatory marker C-Reactive Protein (CRP). Thus, sCD40L may be used alone as a predictor future adverse cardiovascular disorders or in combination with prior art predictors such as cholesterol and CRP. Thus, the present invention does not involve simply duplicating a measurement that previously could be made using other predictors. Instead, levels-of sCD40L are additive to prior art predictors.

As mentioned above, these discoveries have led to new diagnostic tests.

According to one aspect of the invention, a method is provided for characterizing an individual's risk profile of developing a future cardiovascular disorder. The method involves obtaining a level of sCD40L in the individual. The level of sCD40L then is compared to a predetermined value, and the individual's risk profile of developing a future cardiovascular disorder then is characterized based upon the level of sCD40L in comparison to the predetermined value.

The predetermined value can be a single value, multiple values, a single range or multiple ranges. Thus, in one embodiment, the predetermined value is a plurality of predetermined marker level ranges, and the comparing step comprises determining in which of the predetermined marker level ranges the individual's level falls. In preferred embodiments, a preferred predetermined sCD40L value is about or above 2.9 ng/mL of blood. Another preferred predetermined sCD40L value is about or above 3.2 ng/mL of blood. A further preferred predetermined sCD40L value is about or above 5.5 ng/mL of blood. When ranges are employed, it is preferred that one of the plurality of ranges be below about 2.9 ng/mL of blood and that another of the ranges be above about 2.9 ng/mL of blood.

In certain embodiments the individual is an apparently healthy, non-smokoing individual. In some embodiments, the individual is not otherwise at an elevated risk of a myocardial infarction or stroke.

In some embodiments of this aspect of the invention, the cardiovascular disorder is associated with atherosclerotic disease. In some embodiments, the cardiovascular disorder is other than fatal myocardial infarction. In some embodiments, the cardiovascular disorder is a stroke.

According to still another aspect of the invention, a method is provided for characterizing an individual's risk profile of developing a future cardiovascular disorder associated with atherosclerotic disease. A level of sCD40L in the individual is obtained. The level of sCD40L is compared to a predetermined value. The individual's risk profile of developing the future cardiovascular disorder associated with atherosclerotic disease, then is characterized based upon the level of sCD40L in comparison to the predetermined value. The predetermined value can be as described above. The individual characterized may be any individual, but preferably is an apparently healthy individual. The apparently healthy individual can be a smoker or a nonsmoker. In certain embodiments the subject does not otherwise have an elevated risk of an adverse cardiovascular disorder. In certain embodiments, the future cardiovascular disorder associated with atherosclerotic disease does not include a fatal myocardial infarction. The preferred markers and predetermined values are as described above. In one important embodiment, the cardiovascular disorder is stroke. In another important embodiment, the cardiovascular disorder is myocardial infarction. In another important embodiment, the cardiovascular disorder is peripheral artery disease. In a further important embodiment, the cardiovascular disorder is non-fatal myocardial infarction.

According to another aspect of the invention, a method is provided for characterizing an apparently healthy, non-smoking individual's risk profile of developing a future myocardial infarction. The method involves obtaining a level of sCD40L in the individual. The level of sCD40L then is compared to a predetermined value, and the individual's risk profile of developing a future myocardial infarction then is characterized based upon the level of sCD40L in comparison to the predetermined value. In certain embodiments, the individual does not otherwise have an elevated risk of an adverse cardiovascular event.

As in the previous aspect of the invention, the predetermined value may be a single value, a plurality of values, a single range or a plurality of ranges. In one embodiment, the predetermined value is a plurality of predetermined marker level ranges and the comparing step involves determining in which of the predetermined marker level ranges the individual's level falls. Preferred predetermined values and the like for sCD40L are as described above.

According to another aspect of the invention, a method is provided for characterizing an individual's risk profile of developing a future cardiovascular disorder associated with atherosclerotic disease. A level of sCD40L in the individual is obtained. The level of sCD40L is compared to a predetermined value. The individual's risk profile of developing the future cardiovascular disorder associated with atherosclerotic disease, then is characterized based upon the level of sCD40L in comparison to the predetermined value. As in the previous aspect of the invention, the predetermined value may be a single value, a plurality of values, a single range or a plurality of ranges. In one embodiment, the predetermined value is a plurality of predetermined marker level ranges and the comparing step involves determining in which of the predetermined marker level ranges the individual's level falls. Preferred predetermined values and the like for sCD40L are as described above.

The individual characterized may be any individual, but preferably is an apparently healthy individual. The apparently healthy individual can be a smoker or a nonsmoker. In certain embodiments the subject does not otherwise have an elevated risk of an adverse cardiovascular event. In certain embodiments, the future cardiovascular disorder associated with atherosclerotic disease does not include a fatal myocardial infarction. The preferred markers and predetermined values are as described above. In one important embodiment, the cardiovascular disorder is stroke. In another important embodiment, the cardiovascular disorder is myocardial infarction. In another important embodiment, the cardiovascular disorder is peripheral artery disease. In a further important embodiment, the cardiovascular disorder is non-fatal myocardial infarction.

According to still another aspect of the invention, a method is provided in which one uses a blood sCD40L level together with a cholesterol fraction or C-Reactive Protein (CRP) for characterizing an individual's risk profile of developing a future cardiovascular disorder associated with atherosclerotic disease. A level of sCD40L in the individual is obtained. The level of the sCD40L is compared to a first predetermined value to establish a first risk value. A level of a cholesterol or CRP in the individual also is obtained. The level of the cholesterol or CRP in the individual is compared to a second predetermined value to establish a second risk value. The individual's risk profile of developing the cardiovascular disorder then is characterized based upon the combination of the first risk value and the second risk value, wherein the combination of the first risk value and second risk value establishes a third risk value different from the first and second risk values. In particularly important embodiments, the third risk value is greater than either of the first and second risk values. The preferred individuals for testing, markers and predetermined values are as described above. The cardiovascular disorder can be any cardiovascular disorder associated with atherosclerotic disease, although in certain important embodiments the cardiovascular disorder is nonfatal myocardial infarction or ischemic stroke According to yet another aspect of the invention, a method is provided for evaluating the likelihood that an individual will benefit from treatment with an agent for reducing the risk of a cardiovascular disorder, and particularly cardiovascular disorders associated with atherosclerotic disease. The agent can be selected from the group consisting of anti-inflammatory agents, anti-thrombotic agents, anti-platelet agents, fibrinolytic agents, lipid reducing agents, direct thrombin inhibitors, and glycoprotein II b/IIIa receptor inhibitors and agents that bind to cellular adhesion molecules and inhibit the ability of white blood cells to attach to such molecules (e.g. anti-cellular adhesion molecule antibodies). To practice the method, a level of sCD40L in an individual is obtained. This level then is compared to a predetermined value, wherein the level of sCD40L in comparison to the predetermined value is indicative of the likelihood that the individual will benefit from treatment with the agent. The individual then can be characterized in terms of the net benefit likely to be obtained by treatment with the agent.

As mentioned above, the invention is particularly adapted to determining which individuals will preferentially benefit from treatment with an agent for reducing the risk in the individuals of a cardiovascular disorder such as a future stroke or a future myocardial infarction, including nonfatal myocardial infarctions. It also permits selection of candidate populations for clinical trials and for treatment with candidate drugs, by identifying, for example, the individuals most likely to benefit from a new treatment or from a known treatment with a high risk profile of adverse side effects. Thus, the invention provides information for evaluating the likely net benefit of certain treatments for candidate patients.

The invention also contemplates kits comprising a package including an assay for sCD40L and instructions, and optionally related materials such as number or color charts, for correlating the level of sCD40L as determined by the assay with a risk of developing a future cardiovascular disorder or with other patient criteria as described above. In important embodiments, the kits also include an assay for a cholesterol.

In another aspect of the invention, a method for treating a subject to reduce the risk of a cardiovascular disorder, is provided. The method involves selecting and administering to a subject who is known to have an above-normal level of sCD40L an agent for reducing the risk of the cardiovascular disorder. The agent can be an anti-inflammatory agent (including aspirin and nonaspirin anti-inflammatory agents), an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, an angiotensin system inhibitor, and/or combinations thereof. The agent is administered in an amount effective to lower the risk of the subject developing a future cardiovascular disorder. The preferred subjects are apparently healthy subjects otherwise free of current need for treatment with any one or combination of the foregoing agents. In further important embodiments, the subject treated is a nonhyperlipidemic subject. In another embodiment, the subjects are not at an elevated risk of an adverse cardiovascular event (e.g., subjects with no family history of such events, subjects who are nonsmokers, subjects who are nonhyperlipidemic subjects with normal levels of systemic inflammatory markers), other than having an elevated level of sCD40L.

In certain embodiments, the agent is an anti-inflammatory agent selected from the group consisting of Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids or Zomepirac Sodium.

The invention also involves a method for treating subjects with a lipid reducing agent, to prevent cardiovascular disorders. Such an agent is administered to a subject selected on the basis of having an above-normal level of sCD40L. The agent is administered in an amount effective to lower the risk of the subject developing a future cardiovascular disorder. In one embodiment, the subject already has had a cardiovascular event, such as a heart attack or an angioplasty. In this embodiment, the lipid reducing agent can limit further injury or help prevent restenosis, post-myocardial infarction or post-angioplasty injury. In another important embodiment, the subjects are apparently healthy subjects otherwise free of current need for lipid reducing agent treatment. In important embodiments, the subjects are not an elevated risk of an adverse cardiovascular event, other than having elevated levels of sCD40L. In further important embodiments, the subject treated is a nonhyperlipidemic subject. In any of the foregoing embodiments, the lipid reducing agent may be, but is not limited to, gemfibrozil, cholystyramine, colestipol, nicotinic acid, probucol lovastatin, fluvastatin, simvastatin, atorvastatin, pravastatin, or cerivastatin. In preferred embodiments, the lipid reducing agent is pravastatin.

The invention also involves a method for treating subjects with an agent that binds to a cellular adhesion molecule and that inhibits the ability of white blood cells to attach to such molecules, to prevent cardiovascular disorders. Such an agent is administered to a subject selected on the basis of having an above-normal level of sCD40L. The agent is administered in an amount effective to lower the risk of the subject developing a future cardiovascular disorder. In one embodiment, the subject already has had a cardiovascular event, such as a heart attack or an angioplasty. In this embodiment, the agent that binds to a cellular adhesion molecule and that inhibits the ability of white blood cells to attach to such molecules, may limit further injury or help prevent restenosis, post-myocardial infarction or post-angioplasty injury. In another important embodiment, the subjects are apparently healthy subjects otherwise free of current need for treatment with an agent that binds to a cellular adhesion molecule and that inhibits the ability of white blood cells to attach to such molecules. In important embodiments the subjects are not an elevated risk of an adverse cardiovascular event, other than having elevated levels of sCD40L. In further important embodiments, the subject treated is a nonhyperlipidemic subject.

The invention also involves a method for treating subjects with a calcium channel blocker, to prevent cardiovascular disorders. Such an agent is administered to a subject selected on the basis of having an above-normal level of sCD40L. The agent is administered in an amount effective to lower the risk of the subject developing a future cardiovascular disorder. In one embodiment, the subject already has had a cardiovascular event, such as a heart attack or an angioplasty. In another important embodiment, the subjects are apparently healthy subjects otherwise free of current need for calcium channel blocker treatment. In important embodiments the subjects are not an elevated risk of an adverse cardiovascular event, other than having elevated levels of sCD40L. In further important embodiments, the subject treated is a nonhyperlipidemic subject. In any of the foregoing embodiments, the calcium channel blocker may be but is not limited to, dihydropyridines, phenyl alkyl amines, and/or benzothiazepines. In preferred embodiments, calcium channel blockers useful according to the invention, include, but are not limited to, amrinone, amlodipine, bencyclane, diltiazem, felodipine, fendiline, flunarizine, isradipine, nicardipine, nifedipine, nimodipine, perhexilene, gallopamil, tiapamil and tiapamil analogues (such as 1993RO-11-2933), verapamil, phenytoin, barbiturates, and the peptides dynorphin, omega-conotoxin, and omega-agatoxin, and the like and/or pharmaceutically acceptable salts thereof.

The invention also involves a method for treating subjects with a beta-adrenergic receptor blocker, to prevent cardiovascular disorders. Such an agent is administered to a subject selected on the basis of having an above-normal level of sCD40L. The agent is administered in an amount effective to lower the risk of the subject developing a future cardiovascular disorder. In one embodiment, the subject already has had a cardiovascular event, such as a heart attack or an angioplasty. In another important embodiment, the subjects are apparently healthy subjects otherwise free of current need for beta-adrenergic receptor blocker treatment. In important embodiments the subjects are not an elevated risk of an adverse cardiovascular event, other than having elevated levels of sCD40L. In further important embodiments, the subject treated is a nonhyperlipidemic subject. In any of the foregoing embodiments, the beta-adrenergic receptor blocker may be but is not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitril HCl, 1-butylamino-3-(2,5-dichlorophenoxy)-2-propanol, 1-isopropylamino-3-(4-(2-cyclopropylmethoxyethyl) phenoxy)-2-propanol, 3-isopropylamino-1-(7-methylindan-4-yloxy)-2-butanol, 2-(3-t-butylamino-2-hydroxypropylthio)-4-(5-carbamoyl-2-thienyl)thiazol, 7-(2-hydroxy-3-t-butylaminpropoxy) phthalide.

The invention also involves a method for treating subjects with a cyclooxygenase-2 inhibitor, to prevent cardiovascular disorders. Such an agent is administered to a subject selected on the basis of having an above-normal level of sCD40L. The agent is administered in an amount effective to lower the risk of the subject developing a future cardiovascular disorder. In one embodiment, the subject already has had a cardiovascular event, such as a heart attack or an angioplasty. In another important embodiment, the subjects are apparently healthy subjects otherwise free of current need for cyclooxygenase-2 inhibitor treatment. In important embodiments the subjects are not an elevated risk of an adverse cardiovascular event, other than having elevated levels of sCD40L. In further important embodiments, the subject treated is a nonhyperlipidemic subject. In any of the foregoing embodiments, the cyclooxygenase-2 inhibitor may be, but is not limited to, a phenyl heterocycle, a diaryl bicyclic heterocycle, an aryl substituted 5,5 fused aromatic nitrogen compound, a N-benzylindol-3-yl propanoic acid and/or its derivatives, a 5-methanesulfonamido-1-indanone, a N-benzyl indol-3-yl butanoic acid and/or its derivatives, a diphenyl-1,2-3-thiadiazole, a diaryl-5-oxygenated-2-(5H)-furanone, a 3,4-diaryl-2-hydroxy-2,5-dihydrofuran, a stilbene and/or its derivatives, a diphenyl stilbene, an alkylated styrene, a bisaryl cyclobutene and/or its derivatives, a substituted pyridine, a pyridinyl-2-cyclopenten-1-one, and/or a substituted sulfonylphenylheterocycle.

The invention also involves a method for treating subjects with an angiotensin system inhibitor, to prevent cardiovascular disorders. Such an agent is administered to a subject selected on the basis of having an above-normal level of sCD40L. The agent is administered in an amount effective to lower the risk of the subject developing a future cardiovascular disorder. In one embodiment, the subject already has had a cardiovascular event, such as a heart attack or an angioplasty. In another important embodiment, the subjects are apparently healthy subjects otherwise free of current need for angiotensin system inhibitor treatment. In important embodiments the subjects are not an elevated risk of an adverse cardiovascular event, other than having elevated levels of sCD40L. In further important embodiments, the subject treated is a nonhyperlipidemic subject. In any of the foregoing embodiments, the angiotensin system inhibitor may be, but is not limited to, an angiotensin-converting enzyme (ACE) inhibitor, an angiotensin II antagonist, an angiotensin II receptor antagonist, agents that activate the catabolism of angiotensin II, and/or agents that prevent the synthesis of angiotensin I.

According to another aspect of the invention, a method is provided for evaluating the likelihood that an individual will benefit from treatment with an agent for reducing the risk of a cardiovascular disorder associated with atherosclerotic disease. The agent can be selected from the group consisting of anti-inflammatory agents, anti-thrombotic agents, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), calcium channel blockers, beta-adrenergic receptor blockers, cyclooxygenase-2 inhibitors, angiotensin system inhibitors, and/or combinations of the foregoing agents thereof. To practice the method, a level of sCD40L in an individual is obtained. This level then is compared to a predetermined value, wherein the level of sCD40L in comparison to the predetermined value is indicative of the likelihood that the individual will benefit from treatment with the agent. The individual then can be characterized in terms of the net benefit likely to be obtained by treatment with the agent.

The predetermined value can be as described above.

As mentioned above, the invention is particularly adapted to determining which individuals will preferentially benefit from treatment with an agent for reducing the risk in the individuals of a cardiovascular disorder such as a future stroke or a future myocardial infarction, including nonfatal myocardial infarctions. It also permits selection of candidate populations for clinical trials and for treatment with candidate drugs, by identifying, for example, the individuals most likely to benefit from a new treatment or from a known treatment with a high risk profile of adverse side effects. Thus, the invention provides information for evaluating the likely net benefit of certain treatments for candidate patients.

According to another aspect of the invention, a method for reducing sCD40L levels in a subject to lower the risk of an adverse cardiovascular disorder is provided. The method involves selecting and administering to a subject having elevated levels of sCD40L an agent that reduces sCD40L levels in an amount effective to reduce the sCD40L levels in the subject. In one embodiment, the agent is a lipid reducing agent. The preferred subject is an apparently healthy subject. In some embodiments, the subject is not otherwise at an elevated risk of having an adverse cardiovascular event. In certain embodiments, the subject has elevated C-Reactive Protein (CRP) levels. In some embodiments of this aspect of the invention, the subject is otherwise free of indications calling for treatment with a lipid reducing agent.

According to a further aspect of the invention, a method for evaluating the likelihood for vascular intra-plaque lipid accumulation in an individual at risk of developing a cardiovascular disorder, is provided. The method involves obtaining a level of sCD40L in the individual, comparing the level of sCD40L to a predetermined value, and characterizing the individual's risk profile for vascular intra-plaque lipid accumulation, based upon the level of sCD40L in comparison to the predetermined level. The predetermined value can be a plurality of predetermined sCD40L level ranges and said comparing step comprises determining in which of said predetermined sCD40L level ranges said individual's sCD40L level falls. In certain embodiments, the predetermined value is about 2.5 ng/mL of blood or higher. In some embodiments, the predetermined value is about 3.0 ng/mL of blood or higher. In important embodiments, the predetermined value is a plurality of predetermined sCD40L level ranges, one of said plurality being below about 2.5 ng/mL blood and another of said ranges being about 2.5 ng/mL blood, and said comparing step comprises determining in which of said plurality of predetermined sCD40L level ranges said individual's sCD40L level falls. In further important embodiments, the vascular intra-plaque lipid accumulation occurs in the carotid artery. Other preferred ranges and important embodiments are as described above and below.

According to a further aspect of the invention, methods for preparing medicaments useful in the treatment of cardiovascular conditions, are provided.

These and other aspects of the invention will be described in more detail below in connection with the detailed description of the invention.

DETAILED DESCRIPTION OF THE INVENTION

Figure 1:
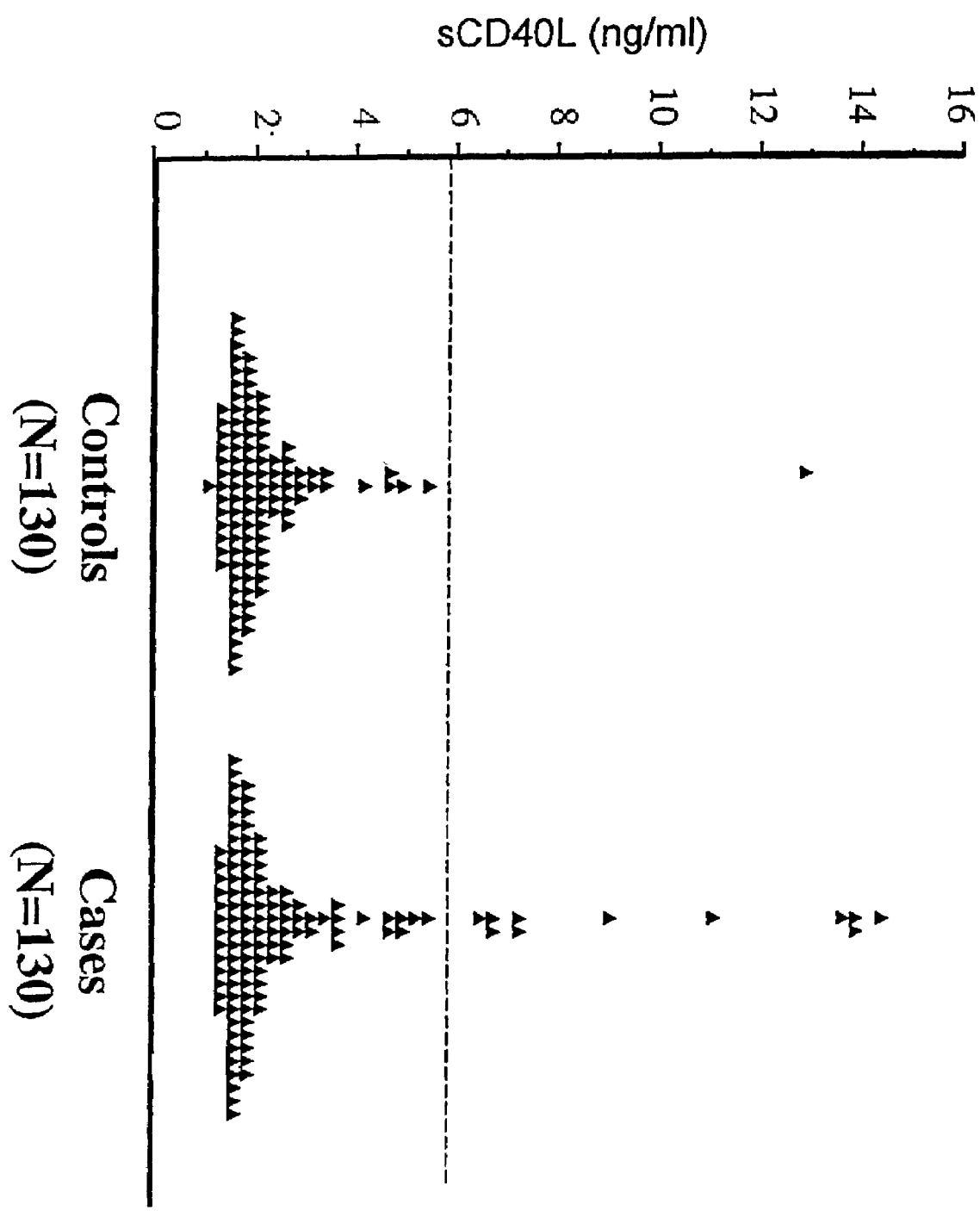
FIG. 1 is a graph demonstrating the relative risk of cardiovascular events in the study population according to sCD40L blood levels. The dotted line depicts the $99^{th}$ percentile cutpoint for the control distribution.

The primary basis for this invention is evidence from a prospective, nested case control analysis among participants in the Women's Health Study (WHS), an ongoing primary prevention trial evaluating the efficiency of vitamin E and low dose aspirin in 28,263 middle aged American women with no history of cardiovascular disease or cancer. In this trial, baseline level of sCD40L, a mediator of inflammation, was found to determine the future risk of myocardial infarction and stroke, independent of a large series of lipid and non-lipid risk factors, and independent of other predictors, including markers of systemic inflammation (see, e.g., U.S. Pat. No. 6,040,147). Specifically, individuals with the highest baseline levels of sCD40L were found to have at least 3 fold increases in risk of developing future cardiovascular events (FIG. 1).

Moreover, in data from the Women's Health Study, the risk of future myocardial infarction and stroke associated with sCD40L, appear to be additive to that which could otherwise be determined by usual assessment of total cholesterol and HDL cholesterol. In this trial, the predictive value of sCD40L was present for non-fatal as well as fatal events, was stable over long periods of time, and was present for non-smokers as well as smokers. Further, data from this trial indicate the magnitude of benefit that apparently healthy individuals can expect from therapeutic agents used in the prevention and treatment of atherosclerotic disorders.

The current invention in one aspect describes the use of sCD40L to predict risk of cardiovascular disorders associated with atherosclerosis such as myocardial infarction and stroke among individuals without current evidence of disease. Thus, these data greatly extend prior observations regarding the use of sCD40L to predict risk among already identified high-risk populations or among symptomatic ischemia patients such as those with unstable angina pectoris. Indeed, since levels of sCD40L increase following acute ischemia, it has been uncertain whether statistical associations observed in prior studies of acutely ill or high-risk populations are casual or due to short-term inflammatory changes, or to interrelations with other risk factors, in particular smoking and hyperlipidemia.

In marked contrast, data from the Women's Health Study indicate for the first time the utility of sCD40L to predict risk among currently healthy and otherwise low-risk individuals, to predict non-fatal as well as fatal events, to predict risk among non-smokers, and to predict risk above and beyond that associated with screening for total and HDL cholesterol. Data from the Women's Health Study also indicate for the first time that the likelihood of efficacy of interventions designed to reduce risk of atherosclerotic events such as myocardial infarction and stroke differs in magnitude based upon a measure of the sCD40L plasma/blood levels. The invention will be better understood with reference to the following brief explanation of terms.

"Cardiovascular myocardial ischemia, disorders" includes myocardial infarction, stroke, myocardial ischemia, angina pectoris and peripheral arteriovascular disease. Cardiovascular disorders do not include venous thrombosis.

"Apparently healthy", as used herein, means individuals who have not previously had an acute adverse cardiovascular event such as a myocardial infarction (i.e., individuals who are not at an elevated risk of a second adverse cardiovascular event due to a primary adverse cardiovascular event). Apparently healthy individuals also do not otherwise exhibit symptoms of disease. In other words, such individuals, if examined by a medical professional, would be characterized as healthy and free of symptoms of disease.

In important embodiments, the subject does not otherwise have an elevated risk of an adverse cardiovascular event. Subjects having an elevated such risk include those with a family history of cardiovascular disease, elevated lipids, smokers, prior acute cardiovascular event, etc. (See, e.g., Harrison's Principles of Experimental Medicine, 15th Edition, McGraw-Hill, Inc., N.Y.—hereinafter "Harrison's"). According to one important aspect of the invention, a method for treating a subject to reduce the risk of a cardiovascular disorder, is provided. The method involves selecting and administering to a subject who is known to have an above-normal level of sCD40L an agent for reducing the risk of the cardiovascular disorder. The agent can be an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, an angiotensin system inhibitor, and/or combinations thereof. The agent is administered in an amount effective to lower the risk of the subject developing a future cardiovascular disorder.

The preferred subjects are apparently healthy subjects otherwise free of current need for treatment with the agent prescribed according to the present invention. For example, if treatment with a particular agent occurs based on elevated levels of sCD40L, then the patient preferably is free of symptoms calling for treatment with that agent (or the category of agent into which the agent falls), other than the symptom of having elevated levels of sCD40L. In some embodiments, the subject is otherwise free of symptoms calling for treatment with any one of any combination of or all of the foregoing categories of agents. Such as, for example, with respect to anti-inflammatory agents, free of symptoms of rheumatoid arthritis, chronic back pain, autoimmune diseases, vascular diseases, viral diseases, malignancies, and the like. In further important embodiments, the subject treated is a nonhyperlipidemic subject. In another embodiment, the subjects are not at an elevated risk of an adverse cardiovascular event (e.g., subjects with no family history of such events, subjects who are nonsmokers, subjects who are nonhyperlipidemic, subjects who do not have elevated levels of a systemic inflammatory marker), other than having an elevated level of sCD40L. In some embodiments, the subject is otherwise free of symptoms calling for treatment with any one of, any combination of or all of the foregoing categories of agents.

In some embodiments, the subject is otherwise free of symptoms calling for treatment with any one of, any combination of or all of the foregoing categories of agents. In further important embodiments, the subject treated is a nonhyperlipidemic subject. A "nonhyperlipidemic" is a subject that is a nonhypercholesterolemic and/or a nonhypertriglyceridemic subject. A "nonhypercholesterolemic" subject is one that does not fit the current criteria established for a hypercholesterolemic subject. A nonhypertriglyceridemic subject is one that does not fit the current criteria established for a hypertriglyceridemic subject (See, e.g., Harrison's Principles of Experimental Medicine, 15th Edition, McGraw-Hill, Inc., N.Y.—hereinafter "Harrison's"). Hypercholesterolemic subjects and hypertriglyceridemic subjects are associated with increased incidence of premature coronary heart disease. A hypercholesterolemic subject has an LDL level of >160 mg/dL, or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject has a triglyceride (TG) level of >250 mg/dL. Thus, a nonhyperlipidemic subject is defined as one whose cholesterol and triglyceride levels are below the limits set as described above for both the hypercholesterolemic and hypertriglyceridemic subjects.

In some embodiments, the subject has normal levels of systemic inflammatory markers. For the purposes of this application, normal such levels means the same things as the absence of elevated levels. Normal levels will depend on the particular systemic inflammatory marker. (See U.S. Pat. No. 6,040,147, incorporated herein in its entirety by reference.)

"Nonsmoking", as used herein, means an individual who, at the time of the evaluation, is not a smoker. This includes individuals who have never smoked as well as individuals who in the past have smoked but presently no longer smoke.

Agents for reducing the risk of a cardiovascular disorder include, but are not limited to, those selected from the group consisting of anti-inflammatory agents, anti-thrombotic agents, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), calcium channel blockers, beta-adrenergic receptor blockers, cyclooxygenase-2 inhibitors, angiotensin system inhibitors, and/or any combinations thereof.

"Anti-inflammatory" agents include but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate;

Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

"Anti-thrombotic" and/or "fibrinolytic" agents include but are not limited to, Plasminogen (to plasmin via interactions of prekallikrein, kininogens, Factors XII, XIIIa, plasminogen proactivator, and tissue plasminogen activator [TPA]) Streptokinase; Urokinase: Anisoylated Plasminogen-Streptokinase Activator Complex; Pro-Urokinase; (Pro-UK); rTPA (alteplase or activase; r denotes recombinant); rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

"Anti-platelet" agents include but are not limited to, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; Anagrelide.

"Lipid reducing" agents include but are not limited to, gemfibrozil, cholystyramine, colestipol, nicotinic acid, probucol lovastatin, fluvastatin, simvastatin, atorvastatin, pravastatin, cerivastatin, and other HMG-CoA reductase inhibitors.

HMG-CoA (3-hydroxy-3-methylglutaryl-coenzyme A) reductase is the microsomal enzyme that catalyzes the rate limiting reaction in cholesterol biosynthesis (HMG-CoA6Mevalonate). An HMG-CoA reductase inhibitor inhibits HMG-CoA reductase, and as a result inhibits the synthesis of cholesterol. A number of HMG-CoA reductase inhibitors has been used to treat individuals with hypercholesterolemia. More recently, HMG-CoA reductase inhibitors have been shown to be beneficial in the treatment of stroke (Endres M, et al., *Proc Natl Acad Sci USA*, 1998, 95:8880–5).

HMG-CoA reductase inhibitors useful according to the invention include, but are not limited to, simvastatin (U.S. Pat. No. 4, 444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273, 995), cerivastatin, and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402, the disclosures of which patents are incorporated herein by reference.

"Direct thrombin inhibitors" include but are not limited to, hirudin, hirugen, hirulog, agatroban, PPACK, thrombin aptamers.

"Glycoprotein IIb/IIIa receptor inhibitors" are both antibodies and non-antibodies, and include but are not limited to ReoPro (abcixamab), lamifiban, tirofiban.

"Calcium channel blockers" are a chemically diverse class of compounds having important therapeutic value in the control of a variety of diseases including several cardiovascular disorders, such as hypertension, angina, and cardiac arrhythmias (Fleckenstein, *Cir. Res.* v. 52, (suppl. 1), p. 13–16 (1983); Fleckenstein, *Experimental Facts and Therapeutic Prospects,* John Wiley, New York (1983); McCall, D., *Curr Pract Cardiol,* v. 10, p. 1–11 (1985)). Calcium channel blockers are a heterogenous group of drugs that prevent or slow the entry of calcium into cells by regulating cellular calcium channels. (Remington, *The Science and Practice of Pharmacy,* Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexilene, gallopamil, tiapamil and tiapamil analogues (such as 1993RO-11-2933), phenytoin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

Cyclooxygenase-2 (COX-2) is a recently identified new form of a cyclooxygenase. "Cyclooxygenase" is an enzyme complex present in most tissues that produces various prostaglandins and thromboxanes from arachidonic acid. Non-steroidal, antiinflammatory drugs exert most of their antiinflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It and was originally identified in bovine seminal vesicles.

Cyclooxygenase-2 (COX-2) has been cloned, sequenced and characterized initially from chicken, murine and human sources (See, e.g., U.S. Pat. No. 5,543,297, issued Aug. 6, 1996 to Cromlish, et al., and assigned to Merck Frosst Canada, Inc., Kirkland, Calif., entitled: "Human cyclooxygenase-2 cDNA and assays for evaluating cyclooxygenase-2 activity"). This enzyme is distinct from the COX-1. COX-2, is rapidly and readily inducible by a number of agents including mitogens, endotoxin, hormones, cytokines and growth factors. As prostaglandins have both physiological and pathological roles, it is believed that the constitutive enzyme, COX-1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar antiinflammatory, antipyretic and analgesic properties to a conventional nonsteroidal antiinflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective "COX-2 inhibitors" are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698, 584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An "angiotensin system inhibitor" is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

"Angiotensin II antagonists" are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., *J. Pharmacol. Exp. Ther.* 247(1), 1–7 (1988)); 4, 5, 6, 7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, Pa.); Losartan (DUP753IMK954, DuPont Merck Pharmaceutical Company); Remikirin (RO42-5892, F. Hoffman LaRoche AG); A$_2$ agonists (Marion Merrill Dow) and certain non-peptide heterocycles (G.D. Searle and Company).

"Angiotensin converting enzyme (ACE), is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

"Renin inhibitors" are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies. Significantly, as is well-known in the art, only a small portion of an antibody molecule, the paratrope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (Frs), which maintain the tertiary structure of the paratope (see, in general, Clar, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves polypeptides of numerous size and type that bind specifically to cellular adhesion molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the cellular adhesion molecule. This process can be repeated through several cycles of reselection of phage that bind to the cellular adhesion molecule. Repeated rounds lead to enrichment of phage bearing particular sequences. DNA sequences analysis can be conducted to identify the sequences of the expressed polypeptides. The minimal linear portion of the sequence that binds to the cellular adhesion molecule can be determined. One can repeat the procedure using a biased library containing inserts containing part of all of the minimal linear portion plus one or more additional degenerate residues upstream or downstream thereof. Yeast two-hybrid screening methods also may be used to identify polypeptides that bind to the cellular adhesion molecules. Thus, cellular adhesion molecules, or a fragment thereof, can be used to screen peptide libraries, including phage display libraries, to identify and select peptide binding partners of the cellular adhesion molecules.

In practicing the methods of the present invention, it is required to obtain a level of sCD40L in an individual. Soluble CD40L is well-known to those of ordinary skill in the art. The level of sCD40L for the individual can be obtained by any art recognized method. Typically, the level is determined by measuring the level of the marker in a body fluid, for example, blood, lymph, saliva, urine and the like. The level can be determined by ELISA, or immunoassays or other conventional techniques for determining the presence of the marker. Conventional methods include sending samples of a patient's body fluid to a commercial laboratory for measurement.

The invention also involves comparing the level of sCD40L for the individual with a predetermined value. The predetermined value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quadrants, the lowest quadrant being individuals with the lowest risk and the highest quadrant being individuals with the highest risk.

The predetermined value can depend upon the particular population selected. For example, an apparently healthy, nonsmoker population with no detectable disease and no prior history of a cardiovascular disorder will have a different 'normal' range of sCD40L than will a smoking population or a population the members of which have had a prior cardiovascular disorder. Accordingly, the predetermined values selected may take into account the category in which an individual falls. Appropriate ranges and categories can be selected with no more than routine experimentation by those of ordinary skill in the art.

The preferred body fluid is blood. For sCD40L, one important cut-off for a population of apparently healthy, nonsmokers is 2.9 ng/mL or below. Another important cut-off for sCD40L is 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0, 10.5 or 11.0 ng/mL. In characterizing risk, numerous predetermined values can be established.

There presently are commercial sources which produce reagents for assays for sCD40L. These include, but are not limited to, BenderMedSystems (Vienna, Austria), and Abbott Pharmaceuticals (Abbott Park, Ill.).

In preferred embodiments the invention provides novel kits or assays which are specific for, and have appropriate sensitivity with respect to, predetermined values selected on the basis of the present invention. The preferred kits, therefore, would differ from those presently commercially available, by including, for example, different cut-offs, different sensitivities at particular cut-offs as well as instructions or other printed material for characterizing risk based upon the outcome of the assay.

As discussed above the invention provides methods for evaluating the likelihood that an individual will benefit from treatment with an agent for reducing risk of a future cardiovascular disorder. This method has important implications for patient treatment and also for clinical development of new therapeutics. Physicians select therapeutic regimens for patient treatment based upon the expected net benefit to the patient. The net benefit is derived from the risk to benefit ratio. The present invention permits selection of individuals who are more likely to benefit by intervention, thereby aiding the physician in selecting a therapeutic regimen. This might include using drugs with a higher risk profile where the likelihood of expected benefit has increased. Likewise, clinical investigators desire to select for clinical trials a population with a high likelihood of obtaining a net benefit. The present invention can help clinical investigators select such individuals. It is expected that clinical investigators now will use the present invention for determining entry criteria for clinical trials.

In another surprising aspect of the invention, it has been discovered that sCD40L has predictive value independent of other known predictors of future adverse cardiovascular disorders. Thus, the present invention does not involve simply duplicating a measurement that previously could be made using other predictors. Instead, levels of sCD40L are additive to prior art predictors. Prior art predictors include markers of systemic inflammation, such as C-Reactive Protein, cytokines, and cellular adhesion molecules. Cytokines are well-known to those of ordinary skill in the art and include human interleukins 1–17. Cellular adhesion molecules are well-known to those of ordinary skill in the art and include integrins, ICAM-1, ICAM-3, BL-CAM, LFA-2, VCAM-1, NCAM, and PECAM. Prior art predictors also include cholesterol.

In a further surprising aspect of the invention, it has been discovered that sCD40L has predictive value on the presence of vascular intra-plaque lipid accumulation in individuals at an elevated risk of developing a cardiovascular disorder. As used herein, individuals "at risk of developing a cardiovascular disorder" are a category of subjects determined according to conventional medical practice. (See, e.g., Harrison's Principles of Experimental Medicine, 15th Edition, McGraw-Hill, Inc., New York). Typically, an individual at risk of developing a cardiovascular disorder has one or more risk factors associated with cardiovascular disease. Such risk factors include family history of a cardiovascular disorder, hypertension, hypercholesterolemia, diabetes, smoking, atherosclerosis, etc. In addition, atrial fibrillation, or recent stroke and/or myocardial infarction are important risk factors. Previously, determination of vascular intra-plaque lipid accumulation in individuals at risk of developing a cardiovascular disorder could only be accomplished using expensive, and in certain cases limiting, technology (e.g., MRI).

It is known in the art that a major factor invoking coronary thrombosis is disruption of an atherosclerotic plaque. As explained elsewhere herein, determining intra-plaque lipid accumulation in individuals at risk of developing a cardiovascular disorder is an important step in determining plaque vulnerability (i.e. plaques at risk of disruption), and thus assessing risk for the future occurrence of a thrombotic event. Studies comparing intact and disrupted plaques have been used to define the characteristics of vulnerable plaques. The characteristics are a lipid core occupying over 50% of overall plaque volume, a thin plaque cap, a large absolute number and density of macrophages, and a reduction in the smooth muscle content of the plaque. Thus, after determining intra-plaque lipid accumulation in individuals at risk of developing a cardiovascular disorder according to the methods of the present invention, one of skill in the art could evaluate whether the plaque is vulnerable and devise appropriate theraputic/interventional regimens to prevent the occurrence of a subsequent thrombotic event in the individual.

The invention also involves a method for treating subjects, with therapies, to prevent cardiovascular disorders. An agent selected from the group consisting of an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, or an agent that binds to cellular adhesion molecules and inhibits the ability of white blood cells to attach to such molecules, and/or any combinations thereof, is administered to a subject who has an above-normal level of a marker of systemic inflammation. The agent is administered in an amount effective to lower the risk of the subject developing a future cardiovascular disorder. In some embodiments the agent is a non-aspirin anti-inflammatory agent. Agents are described elsewhere herein.

An effective amount is a dosage of the agent sufficient to provide a medically desirable result e.g., reduction in risk. The effective amount will vary with the particular condition being treated, the age and physical condition of the subject being treated, the severity of the condition, the duration of the treatment, the nature of the concurrent therapy (if any), the specific route of administration and the like factors within the knowledge and expertise of the health practitioner. For example, an effective amount can depend upon the degree to which an individual has abnormally elevated levels of sCD40L. It should be understood that the agents used according to the invention are intended to lower the risk of a cardiovascular disorder, that is, they are used prophylactically. Thus, an effective amount is that amount which can lower the risk of, slow or perhaps prevent altogether the development of a cardiovascular disorder.

Generally, doses of active compounds would be from about 0.01 mg/kg per day to 1000 mg/kg per day. It is expected that doses ranging from 50–500 mg/kg will be suitable, preferably orally and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The anti-inflammatory agents may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the anti-inflammatory agent, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, intradermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the anti-inflammatory agent into association with a carrier which constitutes one or more accessory ingredients. In general, the compositions are prepared by uniformly and intimately bringing the anti-inflammatory agent into association with a liquid carrier, a finely divided solid carrier, or both, and then, if necessary, shaping the product.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of an agent of the present invention, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854, 480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention will be more fully understood by reference to the following example. This example, however, is merely intended to illustrate the embodiments of the invention and is not to be construed to limit the scope of the invention.

EXAMPLES

Example 1

High Plasma Concentrations of sCD40L are Associated with Increased Vascular Risk in Apparently Healthy Women.

We performed a prospective, nested case control analysis among participants in the Women's Health Study (WHS), an ongoing primary prevention trial evaluating the efficiency of vitamin E and low dose aspirin in 28,263 middle aged American women with no history of cardiovascular disease or cancer.[11] Blood samples were collected in EDTA and stored in liquid nitrogen until analysis For this study, 130 women who subsequently developed either non-fatal myocardial infarction or stroke, or died from acute cardiovascular events during the initial four-year follow-up period were selected as 'case' subjects. A committee of physicians using standardized procedures classified endpoints. For each confirmed case, a 'control' participant of same age (±2 years), similar smoking status (former, current, never) and who remained free of reported cardiovascular disease was selected.

Measurement of baseline plasma sCD40L concentrations used an ELISA (BenderMedSystems; Vienna, Austria). Briefly, diluted (1:5) plasma samples were applied in triplicate to 96-well plates precoated with mouse-anti-human CD40L antibody and mixed (1:2) with a horseradish-peroxidase-labeled secondary mouse-anti-human CD40L antibody (2 h). Subsequently, plates were washed and antibody binding determined by colorimetry employing TMB substrate. Absorbance was read at 650 nm and plasma concentrations of sCD40L determined by comparison with serial dilutions of recombinant human CD40L. The analysis was performed in a blinded fashion. The intra-assay variation among the triplicates for all samples was less than 15 percent. Lipid levels were measured in a laboratory which participates in the Centers for Disease Control Standardization.

Means and proportions for baseline clinical characteristics of the study participants were computed and compared using either Student's T-test or the chi-square statistic. Relative risk of developing future cardiovascular events associated with increasing levels of sCD40L at baseline were then computed in a series of logistic regression analysis which divided the study sample according to the $50^{th}$, $75^{th}$, $90^{th}$, $95^{th}$, and $99^{th}$ percentile cutpoints of the control distribution for sCD40L. All p values are two-tailed and all confidence intervals computed at the 95% level.

Results

Table I shows the baseline clinical characteristics of the study participants. As expected, women who developed cardiovascular disease during follow-up were more likely at study entry to be obese, hypertensive, diabetic, or have a family history of premature atherosclerosis compared to women who remained free of disease. LDL cholesterol and triglyceride levels were higher at baseline among cases, whereas HDL cholesterol levels were lower (all $p \leq 0.01$). Use of hormone replacement therapy did not differ significantly between the two groups.

Overall, plasma levels of sCD40L at baseline among cases exceeded that in controls (2.86±0.35 vs. 2.09±0.19 ng/mL; $p \leq 0.02$). This difference resulted almost completely from an excess of particularly high values among the case subjects. The great majority of cases and control subjects had similar levels of sCD40L at study entry (FIG. 1). However, 11 cases had baseline levels of sCD40L in excess of the $99^{th}$ percentile cutpoint for the control distribution as compared to only 1 study subject in the control group ($p \leq 0.01$).

Relative risks of developing future cardiovascular events, according to the pre-specified cutpoints defined by the distribution of the study controls, rose with increasing concentrations of sCD40L and became statistically significant with levels of sCD40L in excess of the $95^{th}$ and $99^{th}$ percentile cutpoints (RR: 3.29 ($p \leq 0.02$) and 11.83 ($p \leq 0.01$), respectively) (Table II).

An additional post-hoc analysis was performed comparing clinical characteristics among the 12 participants with levels of sCD40L in excess of the $99^{th}$ percentile cutpoint to the 248 participants with lower levels. Age, smoking, body mass index, LDL, and HDL cholesterol levels and hormone replacement therapy were similar between these two study groups (Table III). Study participants with particularly elevated levels of sCD40L had somewhat higher rates of hypertension and a family history of premature coronary artery disease, but neither of these differences achieved statistical significance. None of the 12 women with markedly elevated baseline levels of sCD40L had diabetes. Moreover, there were no significant differences in the time from randomization to the time of the cardiovascular event between the 11 cases with extreme sCD40L levels and the remaining cases with lower sCD40L (15.9 vs. 19.5 months, p=0.3). Assignment to aspirin vs. placebo presumably did not affect our observation, since within the group of 12 subjects showing the highest sCD40L concentrations six were randomly assigned to aspirin and six to placebo. In addition, the bloods assayed for sCD40L were drawn before randomization.

Previous reports on this cohort have documented association between plasma levels of C-reactive protein, IL-6, serum amyloid A and ICAM-1 with increased cardiovascular risk.[12] However, we observed no significant correlation between these parameters and sCD40L.

Discussion

In this prospective, nested case control study of apparently healthy middle aged women, markedly elevated plasma concentrations of sCD40L at baseline ($\geq 5.5$ ng/mL) foretold a significantly increased risk of future cardiovascular events. Previous studies demonstrated that patients with unstable angina had significantly raised serum levels of sCD40L when compared with patients with stable angina and controls.[10] In this circumstance activated platelets and/or T lymphocytes may release sCD40L secondarily. The present study, however, demonstrates elevation of sCD40L concentrations in some women before events that may result from acute thrombosis.

Little is known regarding the mechanisms yielding release of soluble forms of CD40L. Potential source(s) for sCD40L in plasma include platelets and T lymphocytes as well as mononuclear phagocytes and endothelial cells.[1-5] The tendency of family history for cardiovascular disease to correlate with enhanced sCD40L plasma levels suggests that genetic factors, might contribute to our observation. We found no association between sCD40L and C-reactive protein, IL-6, and ICAM-1 levels. It is therefore implied that CD40/CD40L-independent mechanisms may well pertain to women developing cardiovascular complications despite low sCD40L levels. Our discoveries suggest that high plasma concentrations of sCD40L reflect aspects of risk distinct from those gauged by other inflammatory markers.

REFERENCES INCORPORATED IN EXAMPLE 1

1. Alderson M R, Armitage R J, Tough T W, et al. *J Exp Med.* 1993;178:669–74.
2. Reul R M, Fang J C, Denton M D, et al. *Transplantation.* 1997;64:1765–74.
3. Mach F, Schönbeck U, Sukhova G K, et al. *Proc Natl Acad Sci USA.* 1997;94:1931–6.
4. Henn V, Slupsky J R, Grafe M, et al. *Nature.* 1998;391:591–4.
5. Schönbeck U, Libby P. *Cell Mol Life Sci.* 2001;58:4–43.
6. Mach F, Schönbeck U, Sukhova G K, et al. *Nature.* 1998;394:200–3.
7. Schönbeck U, Sukhova G K, Shimizu K, et al. *Proc Natl Acad Sci USA.* 2000;97:7458–63.
8. Lutgens E, Cleutjens K B, Heeneman S, et al. *Proc Natl Acad Sci USA.* 2000;97:7464–9.
9. Graf D, Muller S, Korthauer U, et al. *Eur J Immunol.* 1995;25:1749–54.
10. Aukrust P, Muller F, Ueland T, et al. *Circulation.* 1999;100:614–20.
11. Buring J E, Hennekens C H. *J. Myocard. Ischemia.* 1992;4:19–27.
12. Ridker P M, Hennekens C H, Buring J E, et al. *N Engl J Med.* 2000;342:836–43.

DETAILED DESCRIPTION OF THE DRAWING

FIG. 1. Baseline serum concentrations of sCD40L among middle aged healthy women which either stayed free of (controls, n=130) or developed cardiovascular events (cases, n=130). Samples were analyzed in triplicates, mean values are shown. The dotted line depicts the $99^{th}$ percentile cutpoint for the control distribution.

TABLE I

Baseline characteristics of study participants.

|  | Controls (N = 130) | Cases (N = 130) | P-value |
|---|---|---|---|
| Age, years | 60.3 | 60.3 | Matching criteria |
| Smoking Status (%) |  |  | Matching criteria |
| Current | 26.9 | 26.9 |  |
| Former | 31.6 | 31.6 |  |
| Never | 41.5 | 41.5 |  |
| Body Mass Index (kg/m$^2$) | 25.7 | 27.6 | 0.004 |
| Hypertension (%) | 34.9 | 56.9 | 0.001 |

TABLE I-continued

Baseline characteristics of study participants.

|  | Controls (N = 130) | Cases (N = 130) | P-value |
|---|---|---|---|
| Family history of CAD (%)* | 10.8 | 22.7 | 0.01 |
| Diabetes (%) | 3.1 | 10.8 | 0.02 |
| Current HRT** (%) | 40.0 | 44.6 | 0.1 |
| LDL (mg/dL) | 118.4 | 128.5 | 0.02 |
| HDL (mg/dL) | 48.4 | 42.6 | 0.01 |
| Triglycerides (mg/dL) | 136.5 | 161.0 | 0.01 |
| sCD40L (ng/mL) | 2.09 | 2.86 | 0.02 |

*Before age 60; **HRT, hormone replacement therapy

TABLE II

Baseline characteristics of study participants.

| Cutpoint (percentile) | sCD40L (ng/mL) | Controls % (N) | Cases % (N) | RR | 95% CI | P-value |
|---|---|---|---|---|---|---|
| $50^{th}$ | >1.76 | 50.4 (65) | 50.8 (66) | 1.02 | 0.62–1.65 | 0.95 |
| $75^{th}$ | >2.15 | 24.9 (32) | 30.8 (40) | 1.35 | 0.78–2.33 | 0.29 |
| $90^{th}$ | >2.92 | 10.1 (13) | 17.7 (23) | 1.92 | 0.93–3.98 | 0.08 |
| $95^{th}$ | >3.71 | 5.0 (6) | 13.9 (18) | 3.29 | 1.26–6.59 | 0.02 |
| $99^{th}$ | >5.54 | 0.8 (1) | 8.5 (11) | 11.83 | 1.50–93.0 | 0.01 |

TABLE III

Clinical characteristics of study participants with sCD40L concentrations above $99^{th}$ percentile of the control distribution ($\geq$5.54 ng/mL sCD40L)

|  | sCD40L, >$99^{th}$ (N = 12) | sCD40L, $\geq$$99^{th}$ (N = 248) | P-value |
|---|---|---|---|
| Age, years | 63.1 | 60.2 | 0.3 |
| Smoking Status (%) |  |  | 0.7 |
| Current | 25.0 | 27.1 |  |
| Former | 33.3 | 47.7 |  |
| Never | 41.7 | 31.2 |  |
| Body Mass Index (kg/m²) | 27.3 | 26.7 | 0.7 |
| Hypertension (%) | 58.3 | 45.1 | 0.4 |
| Family history of CAD (%)* | 30.0 | 16.0 | 0.2 |
| Diabetes (%) | 0 | 7.3 | 0.9 |
| Current HRT** (%) | 50.0 | 41.7 | 0.8 |
| LDL (mg/dL) | 126.9 | 127.7 | 0.9 |
| HDL (mg/dL) | 49.8 | 48.4 | 0.7 |
| Triglycerides (mg/dL) | 165.5 | 174.3 | 0.8 |

*Before age 60; **HRT, hormone replacement therapy

Example 2

HMG-CoA Reductase Inhibitors Limit CD40 and CD40L Expression in Human Vascular Cells.

This study tested the hypothesis that HMG-CoA reductase inhibitors (statins) can diminish the expression of the receptor/ligand dyad on these cells in vitro as well as of sCD40L plasma levels in vivo, and that oxidatively modified LDL induces the expression of CD40/CD40L on cells involved in atherosclerosis, namely human vascular EC and SMC, as well as MØ.

Materials and Methods

Materials

Native and oxidized (5 μM $CuSO_4$, 37° C., 24 h) LDL (TBARS: 0.4 and 8.3 nM MDA/mg protein, respectively) were obtained from Biomedical Technologies, Inc. (Stoughton, Mass.). Human recombinant IL-1β, TNFα, and IFNγ were obtained from Endogen (Woburn, Mass.).

Cell Isolation and Culture

Human vascular EC and SMC were isolated from saphenous veins and cultured as described previously.[4,26] Mononuclear phagocytes (MØ) were isolated from leukocyte concentrates by density gradient centrifugation employing Lymphocyte Separation Medium (Organon-Teknika, Durham, N.C.) and were cultured (10 days) in RPMI 1640 (BioWhittaker, Walkersville, Md.) containing 2% human serum (Sigma; St. Louis, Mo.).[26] All cell types were cultured 24 h before and during the experiment in media lacking serum. Viability of the cultures was determined by trypan blue (Sigma, St. Louis, Mo.) exclusion count as well as an oligonucleosome formation assay (Cell Death Detection ELISA, Boehringer Mannheim, Germany).

Reverse Transcription-Polymerase Chain Reaction (RT-PCR)

Total RNA isolated from cultured EC, SMC, or MØ employing RNAzol (Tel-Test; Friendswood, Tex.) was assessed for purity and yield spectrophotometrically (2100 Bioanalyzer, Agilent Technologies, Wilmington, Del.) and was reverse-transcribed (2 μg total RNA; 50 min, 42° C.) employing Superscript II Reverse Transcriptase (LifeTechnologies, Carlsbad, Calif.). PCR was performed for 35 cycles at 95° C. (120 sec), 62° C. (120 sec), and 72° C. (180 sec, 2 sec prolongation per cycle) after hot start, employing primers for CD40 or CD40L previously described.[4] Semi-quantitative PCR studies employing 20, 25, 30, 35, and 40 cycles verified that the conditions used yielded PCR products within the exponential range of amplification and were optimized for signal:background ratios. PCR products were analyzed on ethidium bromide-containing 1.3% agarose gels and visualized by UV transillumination. Loading of equal template amounts was verified by RT-PCR for GAPDH. Mock RT reactions, either lacking reverse transcriptase or employing $H_2O$ as template, demonstrated specificity of the signals obtained.

Western Blot

Culture lysates (50 μg total protein/lane) and supernatants were separated by SDS-PAGE and blotted to polyvinylidene difluoride membranes (Bio-Rad, Hercules, Calif.) using a semi-dry blotting apparatus (3 mA/cm², 30 min; Bio-Rad, Hercules, Calif.). Blots were blocked and primary (mouse-anti-human CD40 or CD40L; both 1:1,000; PharMingen, San Diego, Calif.) antibodies were added in 5% defatted dry milk/PBS/0.1% Tween 20. After 1 h, blots were washed three times (PBS/0.1% Tween 20) and secondary, peroxidase-conjugated, goat-anti-mouse antibody (Jackson Immunoresearch, West Grove, Pa.) was added (1 h). Finally, blots were washed and immunoreactive proteins were visualized using the Western blot chemiluminescence system (NEN™, Boston, Mass.). Data were verified by employing anti-CD40/-CD40L antibodies from Santa Cruz (Santa Cruz, Calif.).

Flow Cytometry

Human vascular EC, SMC, or MØ were washed with ice-cold PBS, harvested by trypsinization, and fixed (PBS/4% paraformaldehyde, 15 min). Subsequently, the cells were washed once with PBS/2% BSA before being incubated (1 h, 4° C.) with either buffer alone or FITC-conjugated control IgG, mouse-anti-human CD40, or mouse-anti-human CD40L antibody (1 μg/ml; PharMingen, San Diego, Calif.). Finally, cells were washed with PBS/2% BSA and analyzed in a Becton Dickinson FACSCAN® flow cytometer employing CELLQUEST® software (Becton Dickinson; San Jose, Calif.). At least 20,000 viable cells per condition were analyzed.

Patient Studies

Whole blood (10 mL) was collected in EDTA from 27 patients presenting for coronary arteriography who had at least a 30% stenosis in one coronary artery. The cohort was divided into patients who were or were not treated with any statin at the time of catheterization. Blood was drawn at baseline (0 month) and final follow-up visit (6 months), and plasma was stored at −70° C. All subjects were studied in the fasting state. Written informed consent was obtained from all subjects and the study was approved by the Human Research Committee of Brigham and Women's Hospital. Plasma lipids as well as IL-1β, IL-6, TNFα, IFNγ, sVCAM, C-reactive protein (CRP), and sCD40L were measured by ELISA (Sigma, St. Louis, Mo.; Endogen, Woburn, Mass.; BenderMedSystems, Vienna, Austria). The two groups did not differ significantly in age, gender, diabetes mellitus, smoking, triglycerides, or HDL (Table I). The statin-treated group had significantly lower total cholesterol and LDL, as expected.

Ex vivo Fibrin Clot Formation

Blood was collected from mice by retro-orbital bleeding into 0.1 volume of 0.13M trisodium citrate using non-coated capillary tubes. Platelet-rich plasma (PRP) was prepared by centrifugation (500×g, 5 min, 20° C.) and fibrin clot formation was examined using a modification of a microtiter-plate clot lysis assay described previously.[27] Clots were prepared with 2.94 μM fibrinogen, 0.24 μM plasminogen, 36 pM t-PA, 3.8 nM thrombin, and 5.3 mM $CaCl_2$ (all final concentrations). PRP (final concentration of 10% (v/v)) was incorporated into clots. Clot formation was monitored at 405 nm for up to 15 min.

Statistical Analysis

Data are presented as mean±SD and groups were compared using the Student's t-test. A value of $p \leq 0.05$ was considered significant.

Results

HMG-CoA Reductase Inhibitors Diminish the Expression of CD40 and CD40L on Human Vascular Endothelial and Smooth Muscle Cells, as Well as Macrophages in vitro Exposure to HMG-CoA reductase inhibitors concentration-dependently diminished the expression of both CD40 and CD40L in human vascular EC, SMC, and MØ. At concentrations >2nM cerivastatin diminished the constitutive as well as IL-1β/TNFα/IFNγ-induced expression of the receptor in EC. Maximal inhibition was achieved at 10–50 nM cerivastatin. Mevalonate reversed the diminished expression of CD40 and CD40L by statins. Parallel studies employing oxLDL as a stimulus or SMC or MØ as the cell type yielded similar results. To determine whether the modulation of the CD40/CD40L expression extends to other statins, parallel experiments employed atorvastatin or simvastatin. These HMG-CoA reductase inhibitors similarly reduced CD40/CD40L expression, but required higher concentrations (100 nM). Re-development of the Western blots with a mouse-anti-human GAPDH antibody, providing similar band-intensities across the blots, verified equal loading among the lanes, and also suggested that statin treatment per se did not affect Western blot analysis. Of note, neither statin affected cell number or viability at the concentrations analyzed (up to 250 nM), as determined by trypan blue exclusion cell count, as well as mono/oligonucleosome formation.

HMG-CoA reductase inhibitors moreover diminished CD40 and CD40L mRNA expression in human vascular EC and MØ stimulated either with pro-inflammatory cytokines (IL-1β/TNFα/IFNγ) or oxLDL. Atorvastatin or simvastatin yielded similar results. Mevalonate reversed the diminished expression of CD40 and CD40L transcripts. Parallel studies analyzing the expression of GAPDH transcripts demonstrated application of equal amounts of reverse transcribed mRNA to each reaction and furthermore suggested that treatment with statins per se did not affect the RT-PCR.

In accord with the findings for whole cell lysates, cerivastatin concentration-dependently diminished the cell surface expression of both CD40 and CD40L on human vascular EC, as well as MØ. Notably, the cerivastatin concentrations required for minimal and maximal reduction in CD40 and CD40L surface expression resembled those observed for whole cell lysates in the Western blot as well as the RT-PCR studies. All three statins acted similarly, but required different concentrations to achieve equal reduction in CD40/CD40L expression (cerivastatin>simvastatin=atorvastatin).

Since CD40L can also be shed as a biologically active soluble form, sCD40L, we tested whether treatment of EC, SMC, and MØ with HMG-CoA reductase inhibitors affected the secretion of sCD40L. Indeed, cerivastatin treatment markedly lowered sCD40L concentrations in culture.

Combined, RT-PCR, Western blot, and FACS studies suggest that oxLDL induces and statins diminish the cell surface expression and/or release of CD40 or CD40L by regulating gene activity rather than intracellular translocation.

HMG-CoA Reductase Inhibitors Diminish sCD40L Plasma Levels in Humans

To assess the potential clinical relevance of these in vitro findings, we performed a pilot study to determine whether treatment of patients with HMG-CoA reductase inhibitors diminished sCD40L plasma levels. Plasma of statin-treated atherosclerotic subjects had significantly lower levels of sCD40L compared to non-treated patients (8.3±3.1 ng/ml (n=11) vs. 13.1±2.5 ng/ml (n=16); p<0.05). The individual sCD40L levels did not vary significantly if the treatment status of the patient at baseline and 6 month follow-up did not change. However, sCD40L plasma levels at 6 month follow-up decreased markedly in patients changed to statin treatment (13.1±5.74 ng/ml vs. 5.21±2.36 ng/ml (n=4); p<0.05). Plasma levels of IL-1β, IL-6, TNFα, IFNγ, and sVCAM-1 did not change with statin treatment. Plasma concentrations of C-reactive protein (CRP) were lower in the statin-treated group, although the difference did not achieve statistical significance.

Oxidized LDL Induces Expression of CD40 and CD40L in Human Vascular Cells

Oxidatively modified LDL (oxLDL) concentration-dependently enhanced the faint constitutive expression of CD40 and CD40L protein in human vascular EC and MØ. Augmentation of basal CD40/CD40L expression on either cell type required 1–3 μg oxLDL/ml. Maximal expression of CD40 (5.1±1.1 fold above non-stimulated control; n=4) and CD40L (4.2±2.2 fold; n=3) immunoreactive protein was achieved with 10–30 μg oxLDL/ml. Native LDL also induced expression of the receptor (2.8±1.1 fold; n=2) and ligand (2.2±0.8 fold; n=2), although to a lesser extent. Furthermore, oxLDL concentration-dependently augmented the expression of CD40 and CD40L mRNA in human vascular EC or MØ. Parallel studies analyzing the expression of GAPDH transcripts demonstrated application of equal amounts of reverse transcribed mRNA amounts to each reaction and furthermore suggested that oxLDL stimulation per se did not affect the RT-PCR.

Deficiency of CD40L Prolongs Time of Coagulation of Murine Blood ex vivo

In light of recent data implicating CD40L in thrombosis and the statin-mediated lowering of plasma sCD40L levels shown above, we further tested the hypothesis that diminished expression, of CD40L affects blood coagulation. Indeed, platelet-rich plasma from CD40L-deficient mice showed delayed coagulation in a fibrin clot formation assay when compared to wildtype mice preparations, supporting a role for CD40L in blood coagulation. These observations on the role of CD40L in blood coagulability provide a pathway by which reduction in CD40 signaling via HMG-CoA reductase inhibitors might reduce thrombotic complications of atherosclerosis.

Discussion

Clinical benefits in patients with average or below average LDL levels and reduced cardiovascular risk independent of the degree of LDL-lowering in a consistent series of previous clinical trials have highlighted the potential clinical relevance of the putative "pleiotropic" effects of statins.[21-24, 28] In addition to their lipid-lowering effects, numerous clinical and experimental studies have suggested anti-inflammatory pathways of statins, such as diminished expression of chemokines, major histocompatibility complex II molecules, matrix-degrading enzymes, and the procoagulant tissue factor, as well as the augmented expression of nitric oxide.[22,23,25,28] Moreover, treatment of Watanabe heritable hyperlipidemic rabbits with HMG-CoA reductase inhibitors diminishes the expression of numerous pro-atherogenic inflammatory mediators in vivo.[29,30] Although statins lowered lipids only modestly in these rabbits lacking LDL-receptors, these in vivo observations could not conclusively distinguish the degree to which effects on lipoproteins account for the anti-inflammatory effects observed. The present report provides evidence for a novel anti-inflammatory pathway by which statins may act both dependently and independently of lipid-lowering. Three members of this drug class (cerivastatin, atorvastatin, or simvastatin) significantly diminished the constitutive as well as cytokine-induced expression of CD40 and CD40L protein and transcript in cell types implicated in atherosclerosis, namely human vascular EC, SMC, and MØ, arguing for a lipid-lowering independent function of statins. However, the identification of oxLDL as an inducer of CD40 and CD40L in these cell types further suggests that statins might affect CD40/CD40L expression, at least in part, also via their lipid-lowering properties. Of note, previous studies have colocalized oxLDL with CD40 and CD40L within early human atherosclerotic lesions,[31] a finding in accord with our hypothesis that oxLDL provides an initial signal for the expression of the CD40 receptor/ligand dyad in atherosclerotic plaques.

The pilot observation that patients treated with statins have diminished levels of sCD40L supports the clinical relevance of the present in vitro observations. Several cell types might give rise to sCD40L. Platelets release sCD40L upon ligation of the thrombin receptor in vitro as well as upon thrombus formation in vivo.[32,33] However, as suggested by our own and other previous studies, other cell types, including EC, MØ, and T lymphocytes, might also generate sCD40L.[11,12,17,18]

The present observation that CD40L-deficient platelet-rich plasma clots more slowly than preparations from wild type mice suggests that CD40L, in its membrane-bound and/or soluble form, modulates thrombosis, a crucial determinant of cardiovascular risk. The finding that CD40L can activate platelets by functioning as an $\alpha_{IIb}\beta_3$ ligand further supports this hypothesis.[35]

REFERENCES INCORPORATED IN EXAMPLE 2

1. Libby P, Hansson G K. *Lab. Invest.* 1991;64:5–15.
2. Ross R. *N Engl J Med.* 1999;340:115–126.
3. Reul R M, Fang J C, Denton M D, et al. *Transplantation.* 1997;64:1765–1774.
4. Mach F, Schönbeck U, Sukhova G K, et al. *Proc Natl Acad Sci USA.* 1997;94:1931–1936.
5. Gaweco A S, Wiesner R H, Yong S, et al. *Liver Transpl. Surg.* 1999;5:1–7.
6. Afford S C, Randhawa S, Eliopoulos A G, et al. *J Exp Med* 1999;189:441–446.
7. Malik N, Greenfield B W, Wahl A F, et al. *J Immunol.* 1996;156:3952–3960.
8. Zhou L, Stordeur P, de Lavareille A, et al. *Thromb. Haemost.* 1998;79:1025–1028.
9. Miller D L, Yaron R, Yellin M J. *J Leukoc Biol.* 1998; 63:373–379.
10. Slupsky J R, Kalbas M, Willuweit A, et al. *Thromb Haemost.* 1998;80:1008–1014.
11. Schönbeck U, Libby P. *Cell Mol Life Sci.* 2001;58:4–43.
12. Schönbeck U, Libby P. *Circ Res.* 2001;89:1092–1103.
13. Mach F, Schönbeck U, Sukhova G K, et al. *Nature.* 1998;394:200–203.
14. Lutgens E, Gorelik L, Daemen M J, et al. *Nat Med.* 1999;5:1313–1316.
15. Schönbeck U, Sukhova G K, Shimizu K, et al. *Proc Natl Acad Sci USA.* 2000;97:7458–7463.
16. Lutgens E, Cleutjens K B, Heeneman S, et al. *Proc Natl Acad Sci USA.* 2000;97:7464–7469.
17. Graf D, Muller S, Korthauer U, et al. *Eur J Immunol.* 1995;25:1749–1754.
18. Ludewig B, Henn V, Schroder J M, et al. *Eur J Immunol.* 1996;26:3137–3143.
19. Aukrust P, Muller F, Ueland T, et al. *Circulation.* 1999;100:614–620.
20. Schönbeck U, Varo N, Libby P, et al. *Circulation.* 2001;104:2266–2268.
21. Vaughan C J, Murphy M B, Buckley B M. *Lancet.* 1996;348:1079–1082.
22. Dangas G, Smith D A, Unger A H, et al. *Thromb Haemost.* 2000;83:688–692.
23. Ni W, Egashira K, Kataoka C, et al. *Circ Res.* 2001;89: 415–421.
24. Heeschen C, Hamm C W, Laufs U, et al. *Circulation.* 2002;105:1446–1452.
25. Kwak B, Mulhaupt F, Myit S, et al. *Nat Med.* 2000;6: 1399–1402.
26. Schönbeck U, Mach F, Sukhova G K, et al. *J Exp Med.* 1999;189:843–853.
27. Robbie L A, Booth N A, Croll A M, et al. *Thromb Haemost.* 1993;70:301–306.
28. Libby P, Aikawa M, Schönbeck U. *Biochim Biophys Acta.* 2000;1529:299–309.
29. Bustos C, Hernandez-Presa M A, Ortego M, et al. *J Am Coll Cardiol.* 1998;32:2057–2064.
30. Aikawa M, Rabkin E, Okada Y, et al. *Circulation.* 1998;97:2433–2444.

31. Hakkinen T, Karkola K, Yla-Herttuala S. *Virchows Arch.* 2000;437:396–405.
32. Henn V, Slupsky J R, Grafe M, et al. *Nature.* 1998;391:591–594.
33. Viallard J F, Solanilla A, Gauthier B, et al. *Blood.* 2002;99:2612–2614.
34. Garlichs C D, John S, Schmeisser A, et al. *Circulation.* 2001;104:2395–2400.
35. Andre P, Prasad K S, Denis C V, et al. *Nat Med.* 2002;8:247–252.

Example 3

Soluble CD40 Ligand Levels Indicate Lipid Accumulation in Carotid Atheroma

A major factor invoking coronary thrombosis is disruption of an atherosclerotic plaque. Studies comparing intact and disrupted plaques have been used to define the characteristics of vulnerable plaques i.e. those at risk of disruption. The characteristics are a lipid core occupying over 50% of overall plaque volume, a thin plaque cap, a large absolute number and density of macrophages, and a reduction in the smooth muscle content of the plaque. Such vulnerable plaques make up a small proportion of all the plaques present in most individuals. Angiographic stenosis, however, does not predict vulnerability because there is no relation between core size or plaque size with stenosis. A large proportion of disruption episodes go unnoticed clinically because the thrombus does not sufficiently encroach on the lumen to cause ischaemia. These subclinical episodes, however, will invoke plaque growth. Plaque disruption is followed by a smooth muscle proliferative repair response analogous to that occurring after angioplasty. In both situations, exuberant repair leads to post event stenosis. Reconstruction of coronary lesions at autopsy shows that 70% of high grade stenosis (angiographic>50% diameter) have had an episode of healed disruption. Such data highlight the role of plaque disruption in the generation of advanced stenotic lesions irrespective of whether an acute clinical event occurred.

In summary, the structure and the dynamic biology of the atheroma, rather than the severity of stenosis, largely determine cardiovascular events. Large lipid pools and thin fibrous caps characterize vulnerable plaque, and inflammatory mechanisms play a pivotal role in determining plaque stability.[12] Much of our knowledge of the unstable atheroma derives from post-mortem examination, and less is known about the relationships of inflammatory mechanisms and lesion structure in vivo.

Evidence from animal studies supports the importance of CD40 ligand as inhibition of CD40 signaling in atherosclerosis-prone mice reduced the size and lipid content of aortic lesions, and yielded a relative increase in smooth muscle content and fibrillar collagen.[9] Moreover, as discussed elsewhere herein (see Example 1), elevated plasma levels of soluble CD40 ligand at baseline predict prospectively cardiovascular events among apparently healthy women.

Recent advances in magnetic resonance imaging (MRI) have permitted non-invasive assessment of carotid plaque composition.[11-13] Specifically, use of a custom-made phased array carotid coil has demonstrated high levels of agreement between carotid MRI findings and results at histology among 22 patients undergoing carotid endarterectomy (89% agreement; kappa=0.83; 95% confidence interval 0.67–1.0).[14] Furthermore, high-resolution carotid MRI accurately detects intra-plaque lipid-rich cores.[12,13,15,16]

This study tested the hypothesis that elevated plasma levels of soluble CD40 ligand correlated with features suggestive of lipid-rich cores on high-resolution carotid MRI.

Methods

We invited men and women with stenoses greater than or equal to 30 percent in either internal or common carotid artery by carotid ultrasonography to participate in the study, from January 2001 to January 2002. Any patient with a pacemaker or implantable cardioverter defibrillator was excluded, as well as patients who had received surgical clips or coronary stents in the previous two months. Patients requiring systemic corticosteroids for a systemic inflammatory condition were also excluded. The study population comprised the 49 consecutive patients who gave informed written consent to participate in the study. The study was approved by the Human Research Committee of Brigham and Women's Hospital.

A detailed medical history including prior cardiovascular history, risk factors, and medication use was recorded by a study physician for each participant. A blood sample was drawn by non-traumatic venipuncture, centrifuged, and the plasma stored in EDTA at −80° C.

MRI protocol: The patients underwent high resolution MRI of the carotid arteries using a dedicated phased array carotid coil (IGC, Inc.) on a 1.5T Signa CV/i MRI scanner (GE Medical Systems, Milwaukee, Wis.). 3D time-of-flight images, moderately proton density weighted images, and fat-suppressed moderately T2-weighted images were obtained. For the 3D time-of-flight sequences, parameters were as follows: echo time (TE) 3.5 ms, repetition time (TR) 33–40 ms, flip angle 25 degrees, bandwidth 15.63 kHz, field of view 12–14 cm, slice thickness 2 mm interpolated to 1 mm, 32 slices, acquired matrix 256×256, reconstructed matrix 512×512, with one excitation. For the moderately proton density weighted sequence a TE of 21–22 ms was used, and for the moderately T2-weighted acquisition a TE of 53–58 ms was used with chemical-selective fat suppression. Parameters for these scans were: TR 2 R-R intervals, echo train length 16, bandwidth 62.5 kHz, field of view 14 cm, slice thickness 3 mm, acquired matrix 256×256, reconstructed matrix 512×512, with one excitation. Slice levels were centered at the carotid bifurcation in each patient. Two board-certified radiologists blinded to all other information determined the presence or absence of intra-plaque lipid, based on the loss of signal between the proton density weighted images and the fat-suppressed moderately-T2 weighted fast spin echo images with iso-intense signal on 3D time-of-flight imaging.[15] The percent diameter stenosis was calculated as the difference between reference and stenotic diameters on 3D time-of-flight axial images, divided by the reference diameter and multiplied by 100. The images were read independently off-line. Inter-observer variability was <10%.

Baseline plasma soluble CD40 ligand concentrations were measured by ELISA as previously described.[10] In brief, 1:5 diluted plasma samples were applied in triplicate to 96-well plates precoated with mouse anti-human CD40 ligand antibody and mixed (1:2) with a horseradish-peroxidase-labeled secondary mouse anti-human CD40 ligand antibody for two hours. Plates were then washed and antibody binding determined by colorimetry using 3,3'-5,5'-tetramethyl benzidine substrate. Absorbance was read at 650 nm and plasma concentrations of soluble CD40 ligand were determined by comparison with serial dilutions of recombinant human CD40 ligand. Intra-assay variation among the triplicates for all samples was less than 10% and inter assay variability was 7.4%.

We divided the study participants into two groups, those with evidence of intra-plaque lipid on carotid MRI, and those without evidence of intra-plaque lipid. Median levels of soluble CD40 ligand were computed and compared between the two groups using Wilcoxon's ranked sum test. Relative risks of having intra-plaque lipid associated with elevated soluble CD40 ligand levels were computed by use of logistic regression models that divided the study sample according to the median level of soluble CD40 ligand among those without evidence of intra-plaque lipid.

accumulations (median 2.54 ng/ml [interquartile range (IQR) 1.85–3.52] vs median 1.58 ng/ml [IQR 1.21–2.39]; p=0.02). In contrast, soluble CD40 ligand levels did not correlate with percent diameter stenosis (r=−0.19; p=0.21). The relative risk for intra-plaque lipid associated with soluble CD40 ligand levels above the median was 6.0 (95% confidence interval 1.15–31.23; p=0.03). The magnitude of this predictive effect did not substantially change when analyzed by a multivariable model controlling for the effects of gender, diabetes, hypertension, current smoking, percent stenosis, and ratio of total cholesterol to high density lipoprotein cholesterol (relative risk 5.12, 95% confidence interval 0.78–33.73; p=0.09).

TABLE IV

Baseline Clinical Characteristics of the Study Population.

|  | Total Cohort (n = 46) | No Intra-plaque lipid Group 1 (n = 32) | Intra-plaque lipid Group 2 (n = 14) | P value (Group 1 vs Group 2) |
|---|---|---|---|---|
| Age (years) mean ± SD | 70.5 ± 8.1 | 71.0 ± 7.9 | 69.4 ± 8.8 | 0.5 |
| Male Gender | 31/46 (67.4%) | 24/32 (75%) | 7/14 (50%) | 0.10 |
| History of Diabetes | 15/46 (32.6%) | 7/32 (21.9%) | 8/14 (57.1%) | 0.02 |
| History of Hypertension | 37/46 (80.4%) | 24/32 (75%) | 13/14 (92.9%) | 0.16 |
| Current Smoker | 5/46 (10.9%) | 2/32 (6.3%) | 3/14 (21.4%) | 0.13 |
| History of High Cholesterol | 34/46 (73.9%) | 23/32 (71.9%) | 11/14 (78.6%) | 0.6 |
| Prior TIA or Stroke | 13/46 (28.3%) | 8/32 (25%) | 5/14 (35.7%) | 0.46 |
| Statin use | 31/46 (67.4%) | 20/32 (62.5%) | 11/14 (78.6%) | 0.28 |
| Percent diameter stenosis | 57% ± 23 | 56% ± 24 | 58% ± 20 | 0.6 |
| Soluble CD40 ligand (ng/ml) median [interquartile range] | 1.89 [1.35 – 2.64] | 1.58 [1.21 – 2.39] | 2.54 [1.85 – 3.52] | 0.02 |

TIA = transient ischemic attack

Results

Of the 49 patients enrolled, carotid MRI images could not be obtained for 3 patients due to claustrophobia. We utilized the observations for analyses of the remaining 46 patients. The baseline clinical characteristics of the patients (Table IV) revealed that there was a high prevalence of a history of hypertension, diabetes, and hypercholesterolemia in the overall study cohort. Thirteen of the 46 patients (28.3%) had a prior history of transient ischemic attack (TIA) (n=8) or stroke (n=6); one patient had suffered both TIA and stroke. The remaining 33 patients (71.7%) were asymptomatic.

Fourteen patients had evidence of intra-plaque lipid and 32 did not. Patients with evidence of intra-plaque lipid more likely had diabetes (p=0.02) than those patients without evidence of intra-plaque lipid. There was also a trend towards an increased proportion of women (p=0.1), patients with a history of hypertension (p=0.16), and current smokers (p=0. 13) in the group with intra-plaque lipid. Mean percent carotid diameter stenosis (58%±20 vs 56%±24) did not differ between those with and without evidence of intra-plaque lipid.

Subjects with intra-plaque lipid had higher baseline levels of soluble CD40 ligand than among those without lipid Discussion As described elsewhere herein (Example 1), baseline plasma levels of soluble CD40 ligand prospectively predict cardiovascular events among apparently healthy women. The current data provide novel insight into the mechanism through which elevated levels of soluble CD40 ligand may reflect future cardiovascular risk in humans. We found an association between elevated plasma levels of soluble CD40 ligand and carotid plaques with features of high risk without relation to the severity of stenosis. These data agree with evidence from studies showing that interruption of CD40 signaling reduced the size and lipid content of aortic lesions in atherosclerosis-prone mice.[9]

Previous work has found that high-resolution carotid MRI, using a similar phased array carotid coil, can accurately predict histological findings of lipid pool following carotid endarterectomy[15]; our MRI protocol relies more on T2-weighted protocols, which other studies have shown can accurately distinguish lipid pool.[12,13,16] The predictive effect of soluble CD40 ligand persisted after adjustment for traditional cardiovascular risk factors, although the confidence intervals did widen in the adjusted analysis, as might be expected given that CD40 ligation appears to represent a common causal pathway in lipid pool formation.

In conclusion, we believe that this study establishes a link between plasma levels of CD40 ligand and intra-plaque lipid, which represents one potentially important marker of plaque vulnerability.

REFERENCES INCORPORATED IN EXAMPLE 3

1. Davies M J. *Circulation* 1996;94:2013–20.
2. Libby P *Circulation* 1995;91:2844–50.
3. Karmann K, et al. *Proc Natl Acad Sci USA* 1995;92: 4342–6.
4. Kornbluth R S, et al. *Proc Natl Acad Sci USA* 1998;95: 5205–10.
5. Mach F, et al. *J Clin Invest* 1999; 104:1041–50.
6. Denger S, et al. *Atherosclerosis* 1999;144:15–23.
7. Mach F, et al. *Circulation* 1997;96:396–9.
8. Schonbeck U, *Am J Pathol* 2000;156:7–14.
9. Schonbeck U, *J Exp Med* 1999;189:843–53.
10. Schonbeck U, *Circulation* 2001;104:2266–8.
11. Fayad Z A, Fuster V. *Circ Res* 2001;89:305–16.
12. Shinnar M, et al. *Arterioscler Thromb Vasc Biol* 1999; 19:2756–61.
13. Serfaty J M, et al. *Radiology* 2001;219:403–10.
14. Hatsukami T S, et al. *Circulation* 2000;102:959–64.
15. Yuan C, et al. *Circulation* 2001;104:2051–6.
16. Toussaint J F, et al. *Arterioscler Thromb Vasc Biol* 1995;15:1533–42.

Equivalents

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A method for characterizing an apparently healthy, non-smoking individual's risk profile of developing a future cardiovascular disorder comprising:

obtaining a level of sCD40L in the individual, comparing the level of sCD40L to a predetermined value, and characterizing the individual's risk profile of developing said future cardiovascular disorder, based upon the level of sCD40L in comparison to the predetermined value.

2. The method of claim 1, wherein the predetermined value is a plurality of predetermined sCD40L level ranges and said comparing step comprises determining in which of said predetermined sCD40L level ranges said individual's sCD40L level falls.

3. The method of claim 1, wherein the individual is not otherwise at an elevated risk of a myocardial infarction or stroke.

4. The method of claim 1, wherein the cardiovascular disorder is associated with atherosclerotic disease.

5. The method of claim 1, wherein the cardiovascular disorder is other than fatal myocardial infarction.

6. The method of claim 1, wherein the predetermined value is about 2.9 ng/mL of blood or higher.

7. The method of claim 1, wherein the predetermined value is about 3.2 ng/mL of blood or higher.

8. The method of claim 1, wherein the predetermined value is about 5.5 ng/mL of blood or higher.

9. The method of claim 1, wherein the predetermined value is a plurality of predetermined sCD40L level ranges, one of said plurality being below about 2.9 ng/mL blood and another of said plurality being above about 2.9 ng/mL blood, and wherein said comparing step comprises determining in which of said plurality of predetermined sCD40L level ranges said individual's sCD40L level falls.

10. The method of claims 1, wherein the cardiovascular disorder is stroke.

* * * * *

UNITED STATES PATENT AND TRADEMARK OFFICE
CERTIFICATE OF CORRECTION

| | | |
|---|---|---|
| PATENT NO. | : 7,189,518 B2 | Page 1 of 1 |
| APPLICATION NO. | : 10/288253 | |
| DATED | : March 13, 2007 | |
| INVENTOR(S) | : Uwe Schönbeck et al. | |

It is certified that error appears in the above-identified patent and that said Letters Patent is hereby corrected as shown below:

In the claims:

Claim 1, (Col. 38, line 37), delete "claims" and replace with --claim--

Signed and Sealed this

Twenty-ninth Day of May, 2007

JON W. DUDAS
*Director of the United States Patent and Trademark Office*